US00PP22141P2

(12) United States Plant Patent
Hall et al.

(10) Patent No.: US PP22,141 P2
(45) Date of Patent: Sep. 13, 2011

(54) RASPBERRY PLANT VARIETY NAMED 'NR7'

(50) Latin Name: ***Rubus idaeus* L.**
Varietal Denomination: NR7

(75) Inventors: Harvey K. Hall, Motueka (NZ); Joseph Stephens, Auckland (NZ)

(73) Assignee: The New Zealand Insitiute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 12/660,434

(22) Filed: Feb. 26, 2010

(51) Int. Cl.
*A01H 5/00* (2006.01)

(52) U.S. Cl. ..... Plt./204

(58) Field of Classification Search ..... Plt./204
See application file for complete search history.

*Primary Examiner* — June Hwu
(74) *Attorney, Agent, or Firm* — Greenlee Sullivan PC

(57) ABSTRACT

A new and distinct floricane fruiting red raspberry, *Rubus idaeus* L., variety is described. The variety results from selection among a population of seedlings derived from the controlled pollination crossing of the raspberry varieties known as HR101 (not patented) and 'Willamette' (not patented). The new variety is distinguished from others by the dwarfing nature of the plant which tends to produce many canes that do not grow more than approximately 600 mm in height. The plant is not suited to commercial fruit production but is very suited to ornamental uses such as in the home garden and containers where it produces attractive foliage and edible raspberry fruit comparable in size to those of taller growing varieties.

4 Drawing Sheets

Genus and species of plant claimed: *Rubus idaeus* L.
Variety denomination: 'NR7'.

BACKGROUND OF THE INVENTION

The new variety of red raspberry, *Rubus idaeus* L., was created in the course of a planned breeding program. 'NR7' was selected as a seedling amongst a family targeted to produce commercial raspberry cultivars. The parents used to make the cross were the unpatented selection HR101 (seed parent) from a Nelson, New Zealand breeding programme and the unpatented variety 'Willamette' (pollen parent).

The controlled cross performed to produce the population from which 'NR7' was selected was carried out in a greenhouse at Nelson, New Zealand in 1997 and resulting seed was sent to Lynden, Wash., USA in 1999. A total of 120 seedlings were raised from the seedlot and were planted. The original plant of the new variety was selected and given the breeders code ZNH062 (and was subsequently coded 'NR7' at the advanced selection stage) during the 2001 summer.

SUMMARY OF THE INVENTION

Key characteristics of 'NR7' are:

(a) A plant that has a dwarf growth habit (FIG. 4).

(b) The ability to form medium-sized firm fruit that are easy to pick, light red in color and ovate-round in shape (FIG. 1), and ripening mid-season.

(c) Completely spineless canes (FIG. 4).

The new variety was first asexually propagated in 2004 in Lynden, Wash. State, USA, being reproduced by tissue culture. The resulting plants propagated true to type, demonstrating that the characteristics of the new cultivar are stable and are transmitted without change through succeeding generations.

The new variety was tested and evaluated during the years 2001 to 2008 in test plots in Lynden, Wash. State, USA.

When compared to the seed parent HR101 the new variety was found to have fruit that were lighter in color and less firm. Also the plant exhibited a dwarf growth habit which is very unusual in red raspberry.

When compared to the pollen parent 'Willamette' the new variety was found to have fruit which were lighter in colour. The plant habit of the new variety is dwarfing with canes consistently less than 0.8 m in height, while 'Willamette' typically produces canes in excess of 1.8 m in height. Another difference between the two varieties is the significantly reduced internode length in the new variety when compared to 'Willamette'. To Applicant's knowledge, no other closely related raspberry varieties display the same dwarfing habit as the claimed plant.

BRIEF DESCRIPTION OF DRAWINGS

The accompanying photographs show typical specimens of the plant, foliage and fruit of the new variety as depicted in colors as nearly true as is reasonably possible to make the same in a color illustration of this character. The photographs were taken on mature plants in Washington State, USA.

DETAILED DESCRIPTION

Horticultural terminology is used in accordance with UPOV guidelines for raspberry. All dimensions in millimeters, weights in grams (unless otherwise stated). Where a color reference is given these refer to The R.H.S. Color Chart, The Royal Horticultural Society, London. 4$^{th}$ Edition, 2001. The specimens described were grown in Lynden, Wash. State, USA and were mature, i.e. two years old.

Environmental data for the Lynden (48.95° N, 122.44° W), Wash., USA growing area demonstrates conditions in spring and early summer (equating to the harvest period for the variety) as follows:

Spring (April/May); mean daily temperature in the range 10-11° C. (mean daily minimum 5.5° C., mean daily maximum 15.5° C.).

Early summer (June/July); mean daily temperature 16° C. (mean daily minimum 10° C., mean daily maximum 21.5° C.).

In winter temperatures below 0° C. are common, the daily mean for December/January is 2.5° C. with the lowest temperature unlikely to be colder than −13° C. Average annual rainfall is approximately 1500 mm.

Figure 2:
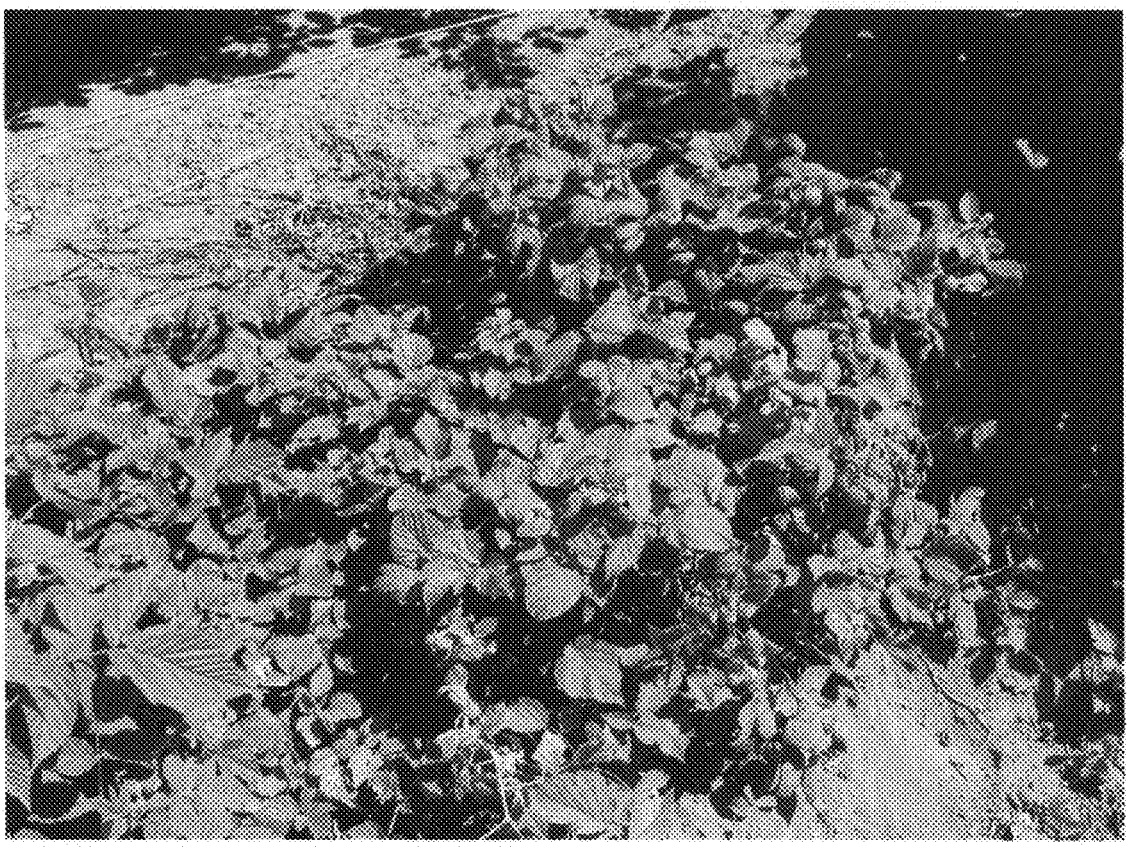
FIG. 2 shows a mature two year old plant of the variety 'NR7'; view includes ripe fruit on the plant and primocane growth
Figure 3:
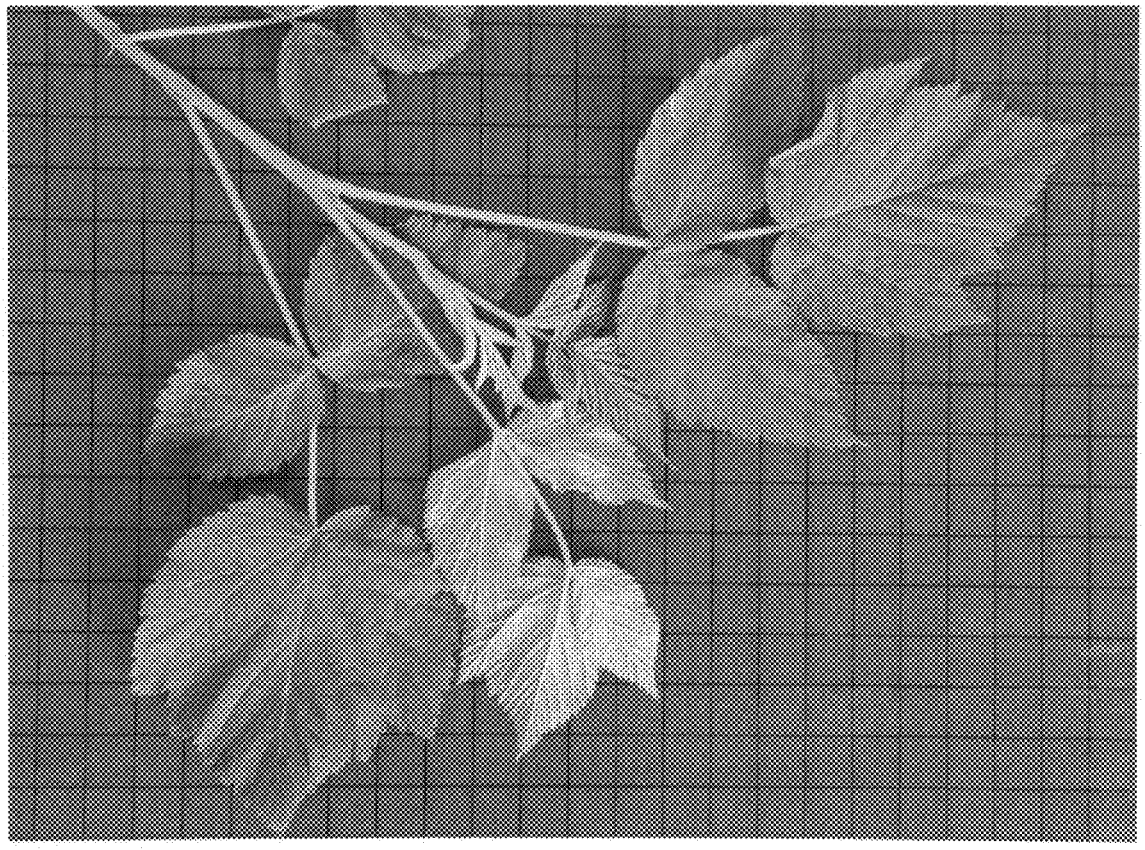
FIG. 3 shows a primocane tip of the plant of the new variety 'NR7'; view shows both the upper and lower leaf surfaces, and both fully expanded and new leaf development
Figure 4:
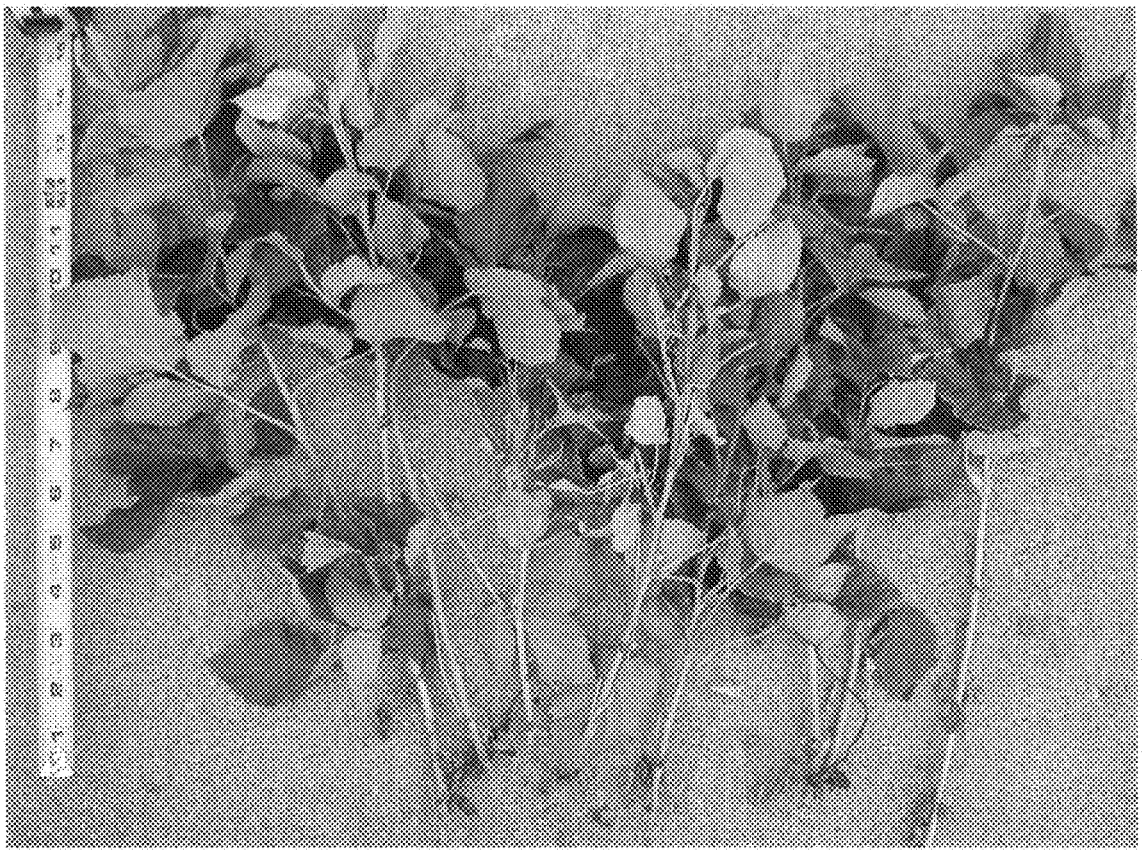
FIG. 4 shows fully grown primocanes of the plant of the new variety 'NR7'; view illustrates the shortened internodes of the stems demonstrating the dwarfing nature of the plant.

Plant and foliage: plants exhibit a very strong dwarf growth habit (FIGS. 2 and 4). Mature plant height is commonly in the range 500-600 mm, although this may vary with the growing conditions. Internode length is typically very short and in the range 10-20 mm. The average spread of the plant is highly dependent on cultural practices but under standard practices it has about a one meter diameter. Plants have high number of young shoots (typically 20-50 per plant) that tend to spread by way of suckers. The new variety is almost completely spineless, the only occurrence of spines are some small spines on the pedicles Canes are pubescent indicating the presence of gene H. Canes typically show light grey-brown coloration near Grey-brown 199B in winter. During the growing season generally the color on the canes is near Yellow-green 144B and there is no anthocyanin evident on the sun-exposed side of the cane. Young shoots are erect and are near Yellow-green 144A in color with some anthocyanin in expanding leaves. The leaves are compound, moderately strongly crinkled, concave and moderately dull, with strong silver coloration on the leaf underside (FIG. 3). The number of primocane leaflets per internode is predominantly three and they are pinnately trifoliate in arrangement. The base of a fully expanded terminal leaflet is concave in shape and typically averages 50-60 mm in diameter and 60-70 mm in length, while the other two leaflets average between 40-60 mm length and 30-35 mm in width. The coloration of the upper surface of the leaflets is green (near Yellow-green 144A on young foliage and near Green 137A on older foliage), the under side being markedly lighter in coloration (near Greyed-green 191C). While the leaves do not have distinguished marginal or vein coloration, the venation has noticeable rises and falls. The leaf petiole typically averages approximately 40-50 mm in length and 2.0 mm in diameter. It is near Yellow-green 144B in color. The fruit is borne on the previous year's growth. The fruiting laterals are very short in length, commonly measuring 200-300 mm and are weakly ascending and horizontal.

Inflorescence: white flowers are borne on short slender pedicels. Despite having no spines on canes commonly two very small spines (less than 1 mm wide and less than 1 mm long) are present near the base of the pedicel. In Lynden Wash., USA the date bud burst commences is approximately early March, with fifty percent of buds burst by mid March. The time of bloom is mid season for a summer-fruiting raspberry, with peak flowering mid-late May. Flowers are numerous and borne on a paniculate inflorescence. Typically there are five petals, elongated ovate in shape with a rounded apex and flat base. The petals average approximately 7.0-8.0 mm in length and 3.5-4.0 mm in width. They are typically smooth in texture, have a smooth margin and are near White 155C in color. The pedicel length averages approximately 20-25 mm long and approximately 1.0 mm in diameter and is near Yellow-green 144B in color and has weak anthocyanin coloration on the sun-exposed side (near Red-purple 59A). The peduncle is on average 25-30 mm long, and 0.9-1.2 mm wide, with a colouration equivalent to the pedicle. A typical king flower diameter is approximately 20-25 mm (from sepal tip to sepal tip i.e. the widest part of the flower). The flowers are predominantly borne singly or in pairs, although sometimes in clusters of three or more. Terminal branch flower clusters frequently consist of two flowers and basal flower clusters may number three to five. The flowers have no discernible fragrance. Five sepals are present. These are green in coloration (near Grey-green 194B on the bottom and near Yellow-green 144B on top) and on average measure approximately 9 mm in length from base to tip. The reproductive organs are typical for flowers of *Rubus idaeus* L.; the stigmas average approximately 70 in number and are near Yellow-green 145D in color; there are approximately 80-90 stamens the filaments of which are near White 155C in color and average 3.2 mm in length. Anthers are brown and (depending on maturity) near Brown 200B in color.

Harvest: fruit commences ripening typically in late June or early July in Washington USA. Fifty percent of the harvest is typically completed by 15 July, and the main harvest period is complete by late July. Due to its dwarfing habit the plant produces an associated lower yield of fruit compared with taller growing varieties.

Figure 1:
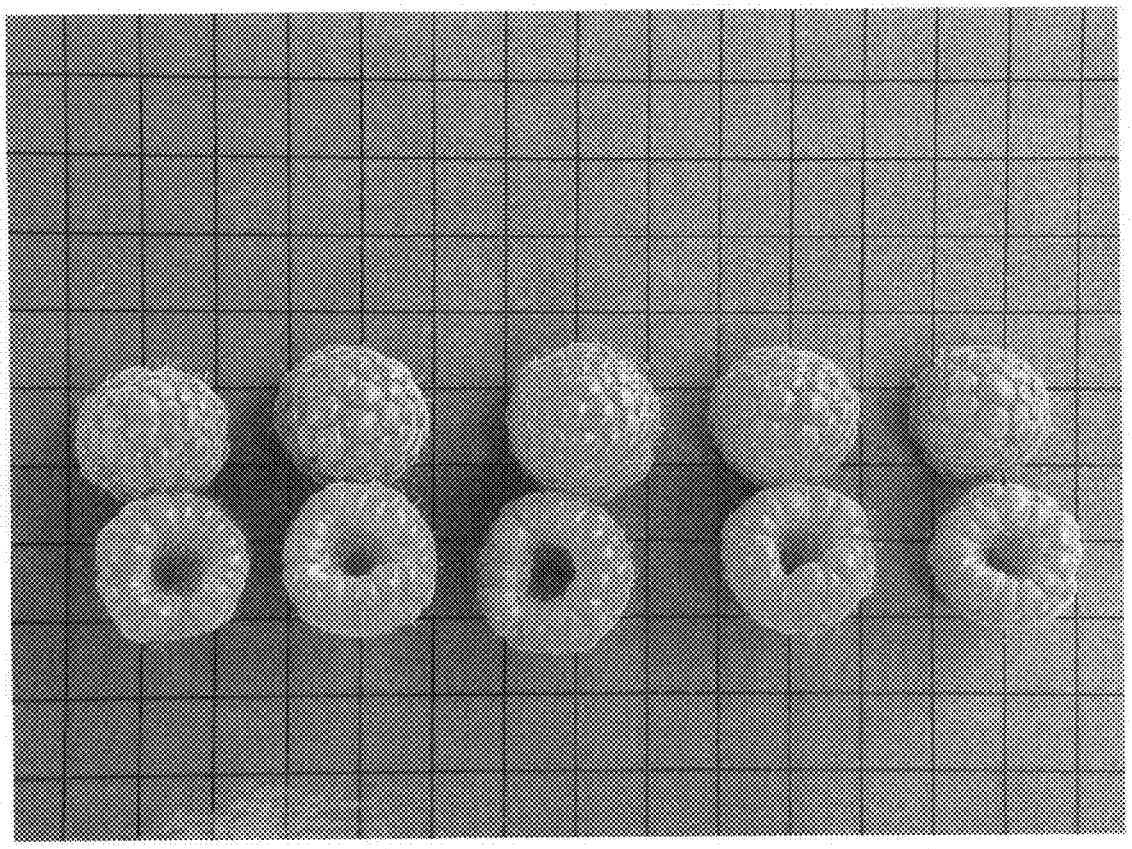
FIG. 1 shows ripe fruit of the variety 'NR7' on a 1 cm grid; view includes fruit tip and collar conformation

Fruit: Fruit is produced on previous year's cane in summer. Berry size is medium. The average berry weight is approximately 4.4 g; individual fruit ranging between 3-5 g in weight. Fruit shape is ovate-round; on the basis of fruit length to width ratio, fruit is slightly longer than broad (FIG. 1). On average berries are 21.7 mm long and 20.4 mm wide at the widest point. Fruit color is medium-light red; external color near Red 46A; internal color near Red 46A. Fruit are considered to be moderately dull. Fruit drupelet size has been observed to be medium (typically 4.0 mm in diameter) and drupelet number typically averages 70 per fruit. The berries are moderately soft and of medium raspberry flavor compared with fruit produced by other mid-season varieties. Soluble solids concentration is medium to low (typically 6-8° Brix). The seeds average 2.6 mm long and 1.4 mm wide, and are near Greyed-orange N170D in color when dry. Seed numbers per fruit average 70 and weigh on average 0.100 g per fruit (or average 2.0 mg individually).

Pest and disease resistance: Since the selection of this clone in 2001 numerous tests for Raspberry Bushy Dwarf Virus (RBDV) have been carried out on 'NR7' in the USA using enzyme-linked immunosorbent assay (ELISA) and RBDV has never been detected in trial plots of 'NR7'. The parent of 'NR7' has also never tested positive to RBDV and from this we suggest that 'NR7' is resistant to RBDV found in the USA. Resistance to aphids is unknown.

Geographical adaptation: observations indicate that the variety is well-suited to production in regions that offer a medium-high amount of winter chill, for example, 'NR7' performs well in USDA Plant Hardiness zones 8-10 (published as the 2003 US National Arboretum "Web Version" of the USDA Plant Hardiness Zone Map USDA Miscellaneous Publication No. 1475, Issued January 1990).

We claim:

1. A new and distinct red raspberry plant as herein illustrated and described.

* * * * *